United States Patent [19]

Bernstein

[11] 4,439,427

[45] Mar. 27, 1984

[54] METHOD AND COMPOSITION FOR TREATING PEDICULOSIS

[75] Inventor: Joel E. Bernstein, Deerfield, Ill.

[73] Assignee: Soft Sheen Products, Inc., Chicago, Ill.

[21] Appl. No.: 434,858

[22] Filed: Oct. 18, 1982

[51] Int. Cl.³ .................... A61K 31/27; A61K 31/685
[52] U.S. Cl. .................................... 424/199; 424/221; 424/263; 424/300; 424/324; 424/329
[58] Field of Search ............... 424/211, 221, 300, 324, 424/329, 199, 263

[56] References Cited

U.S. PATENT DOCUMENTS 4,112,082  9/1978  Ashani et al. ....................... 424/209

OTHER PUBLICATIONS

Cutting—Handbook of Pharmacology (textbook), 4th Ed., 1969, pp. 570–575.
Chemical Abstracts 81:126794c (Jacob et al.), 1974.
Merck Index, 9th Ed., 1976, pp. 52, 378, 463, 464, 678, 841 & 1034.

*Primary Examiner*—Leonard Schenkman
*Attorney, Agent, or Firm*—Emrich & Lee and Brown, Hill, Dithmar, Stotland, Stratman & Levy

[57] ABSTRACT

A method of treating lice infestations in patients in need of such treatment and composition useful therefor is disclosed and includes topically applying to the lice-infected area an effective amount of one or more of the pediculocide agents selected from the class consisting of the acid salts of demecarium, echothiopate, edrophonium, neostigmine, pyridostigmine and ambenonium; and isoflurophate; and for a time of at least about 3 to 5 minutes to interrupt the breeding cycle of the lice.

20 Claims, No Drawings

METHOD AND COMPOSITION FOR TREATING PEDICULOSIS

BACKGROUND OF THE INVENTION

Lice have constituted a "plague" on mankind for many centuries. There are essentially three main types of infestation by lice specific for the human host: 1. Pediculosis Capitis 2. Pediculosis Corporis and 3. Pediculosis Pubis. Head and body infestations are caused by two different types of Pediculosis humanus. Public infestations are caused by Phthirus pubis. As the lice feed on human skin, they inject their digestive juices and fecal material into the skin. These materials, as well as the puncture wound itself, cause pruritus. The adult female louse has a lifespan of about one month and lays up to ten eggs a day which are firmly attached to hair. These hatch in about seven to nine days and become mature in another week. Currently utilized therapies for pediculosis all involve application of toxic pesticides to the scalp or body. Agents such as lindane and DDT form the first line of therapy for pediculosis. These agents are potent neurotoxins, as well as carcinogens, and are thus far from desirable agents.

I have surprisingly discovered that several commonly utilized eye drops for the treatment of glaucoma, as well as several systemically administered drugs used to control the disease myasthenia gravis, can be incorporated into creams, ointments, solutions and shampoos for topical application, and in such form are effective agents for the eradication of lice infestations of all types. The drugs which I have discovered to be particularly effective in the eradication of lice include demecarium bromide, echothiophate iodide, isoflurophate, neostigmine bromide, and neostigmine methylsulfate. Less effective than these primary agents of choice are edrophonium chloride, pyridostigmine bromide, and ambenonium chloride. The origin of my use of these agents for the treatment of Pediculosis was based upon my observations that first, I had never seen a patient with myasthenia gravis infested with lice, and second, that patients with Pediculosis pubis and glaucoma never had lice in their eyelashes, no matter how severe the pubic involvement.

SUMMARY OF THE INVENTION

It is a general object of the present invention to provide a topical composition and method for treating lice infestations pediculosis capitis, pediculosis corporis and pediculosis pubis whether the lice infestation is caused by pediculosis humanus or phthirus pubis by applying a suitable compound to the infected area which is less toxic than lindane or DDT.

Another object of the present invention is to provide a method of treating lice infestations in patients in need of such treatment and compositions useful therefor comprising topically applying to the lice-infected area an effective amount of one or more of the pediculocide agents selected from the class consisting of the acid salts of demecarium, echothiopate, edrophonium, neostigmine, pyridostigmine and ambenonium; and isoflurophate; and combinations thereof for a time sufficient to interrupt the breeding cycle of the lice.

Another object of the present invention is to provide a method for the topical treatment of lice infestations in patients in need of such treatment and compositions useful therefor comprising a pharmaceutically acceptable carrier of a cream, ointment, solution or shampoo having one or more of the pediculocide agents selected from the class consisting of the acid salts of demecarium, echothiopate, and neostigmine; and isoflurophate; and combinations thereof, said pediculocide agent being present in an amount not less than about 0.01 percent by weight of the carrier.

DETAILED DESCRIPTION OF THE PREFERRED EMBODIMENT

I have investigated the effects of topically applied formulations containing demecarium bromide, echothiophate iodide, isoflurophate, neostigmine bromide, neostigmine methylsulfate, edrophonium chloride, pyridostigmine bromide, and ambenonium chloride on human louse infections by having patients affected with such infestations apply some of these compositions. Additionally, other of these topical formulations were evaluated by exposing live nits to these products, and counting the number of lice which hatched from the nits over the next 14 days.

In the practice of this invention, concentrations of demecarium bromide, echothiophate iodide, isoflurophate, edrophonium chloride, neostigmine bromide, neostigmine methylsulfate, pyridostigmine bromide, and ambenonium chloride ranging from 0.01% to 5.0% were incorporated into creams, lotions, solutions and shampoos and applied to the hair of subjects afflicted with lice infestations or applied to isolated nits on hairs in vitro.

In general the acid salts of demecarium, echothiophate, edrophonium, neostigmine, pyridostigmine and ambenonium as well as isoflurophate are useful in the practice of this invention. The carrier can be any pharmaceutically acceptable agent which is suitable for topical application to the skin and may include emolluents, emulsifiers, stabilizers, softeners, perfume, coloring agents, and the like. If the antipediculocide effective ingredient is present in an amount of less than about 0.01% by weight of the carrier, the reproductive cycle may not be interrupted, whereas if the effective ingredient is present in an amount substantially greater than 5% by weight of the carrier then at least for isoflurophate human toxicity may be a problem, the preferred range being from about 0.1 to about 5% by weight of the carrier.

In every case the antipediculocide ingredient must remain in contact with the nits for a short time with at least three or five minutes being preferred in order to obtain superior results. Leaving the antipediculous agent in contact with the affected area for three to five minutes results in a cure with only a single application, which is a significant advantage over the soaps and shampoos now available which require repeated treatments. Further, the subject process and composition has the added significant feature of not exposing the patient to the toxic effects of DDT or lindane.

EXAMPLE 1

A topical antipediculocide prepared by incorporating 0.125% demecarium bromide into a lotion (containing water, mineral oil, petrolatum, sorbitol, lanolin, lanolin alcohol, stearic acid, triethanolamine, cetyl alcohol, fragrance, butylparaben, methylparaben, propylparaben and sodium chloride) was applied to the pubic hair of a 39 year old male afflicted with pediculosis pubis. The lotion was removed by showering 8 hours after application. No evidence of reinfection was later noted.

EXAMPLE 2

Echothiophate iodide 2% was incorporated into a commercially available shampoo. A 12 year old male with pediculosis capitis utilized this shampoo to wash his hair, leaving the shampoo on the hair for 10 minutes before rinsing. One treatment was sufficient for elimination of the infestation.

EXAMPLE 3

Isoflurophate 0.025% was incorporated into the same lotion vehicle in Example 1, and 5 nits obtained from the hair of a louse infected individual exposed to this lotion in a petri dish. During 14 days of observation after such treatment no lice hatched from the nits.

EXAMPLE 4

Neostigmine methylsulfate 0.05% was incorporated into the same lotion vehicle as described in Example 1, and 5 nits obtained from the hair of a louse infected individual exposed to this lotion in a petri dish. During 14 days of observation after such treatment no lice hatched from the nits.

EXAMPLE 5

Pyridostigmine bromide 5.0% was incorporated into a commercially available shampoo. A 8 year old female with pediculosis capitis utilized this shampoo to wash her hair, leaving the shampoo on the hair for 5 minutes before rinsing. One week later the treatment regimen was repeated. No evidence of reinfestation was noted.

EXAMPLE 6

Neostigmine bromide 0.5% was incorporated into the same lotion vehicle as described in Example 1, and 5 nits obtained from the hair of a louse infected individual exposed to this lotion in a petri dish. During 14 days of observation after such treatment no lice hatched from the nits.

The preferred compounds for use as in antipediculocide are the acids salts of demecarium, echothiopate and neostigmine well as isofluorphate, with the last named compound being least desirable due to its toxicity.

From the foregoing, it has been shown that pediculosis capitis, pediculosis corporis and pediculosis pubis whether caused by pediculosis humanus or phthirus pubis have been effectively treated by the method and composition disclosed herein, and while there has been disclosed what at present is considered to be the preferred embodiments of the present invention, it will be understood that those skilled in the art that various modifications and alterations may be made therein without departing from the true spirit and scope of the present invention, and it is intended to cover in the claims appended hereto all such alterations and modifications.

What is claimed is:

1. A method of treating lice infestations comprising topically applying to the lice-infected area of a subject an effective amount of one or more of the pediculocide agents selected from the class consisting of the acid salts of demecarium, echothiopate, edrophonium, neostigmine, pyridostigmine and ambenonium; isoflurophate; and combinations thereof for a time sufficient to interrupt the breeding cycle of the lice.

2. The method of treating lice infestations set forth in claim 1, wherein the pediculocide is demecarium bromide.

3. The method of treating lice infestations set forth in claim 1, wherein the pediculocide is echothiopate iodide.

4. The method of treating lice infestations set forth in claim 1, wherein the pediculocide is isoflurophate.

5. The method of treating lice infestations set forth in claim 1, wherein the pediculocide is neostigmine bromide.

6. The method of treating lice infestations set forth in claim 1, wherein the pediculocide is neostigmine methylsulfate.

7. The method of treating lice infestations set forth in claim 1, and further comprising a pharmaceutically acceptable carrier having the pediculocide agent disbursed therein and present in the range of from about 0.01 to about 5% by weight of the carrier.

8. The method of treating lice infestations set forth in claim 7, wherein the pediculocide agent is in contact with the lice-infected area in a single application for about five minutes.

9. A method of treating lice infestations comprising topically applying to the lice-infected area of a subject one or more of the pediculocide agents selected from the class consisting of the acid salts of demecarium, echothiopate and neostigmine; isoflurophate; and combinations thereof for a time sufficient to interrupt the breeding cycle of the lice, wherein the pediculocide agent is present in a pharmaceutically acceptable carrier in an amount not less than about 0.01 percent by weight of the carrier.

10. The method of treating lice infestations set forth in claim 9, wherein the carrier is a cream, an ointment, a solution or a shampoo.

11. The method of treating lice infestation set forth in claim 9, wherein the pediculocide agent is present in an amount not less than about 0.1% by weight of the carrier.

12. The method of treating lice infestation set forth in claim 9, wherein the pediculocide agent is present in the range of between about 0.1 and less than about 5% by weight of the carrier.

13. A composition for the topical treatment of lice infestations comprising a pharmaceutically acceptable shampoo having one or more of the pediculocide agents selected from the class consisting of the acid salts of demecarium, echothiopate and neostigmine; isoflurophate; and combinations thereof, said pediculocide agent being present in an amount not less than about 0.01 percent by weight of the carrier.

14. The composition of claim 13, wherein the pediculocide agent is demecarium bromide.

15. The composition of claim 13, wherein the pediculocide agent is echothiopate iodide.

16. The composition of claim 13, wherein the pediculocide agent is isoflurophate.

17. The composition of claim 13, wherein the pediculocide agent is neostigmine bromide.

18. The composition of claim 13, wherein the pediculocide agent is neostigmine methylsulfate.

19. The composition of claim 13, wherein the pediculocide agent is present in the range of from about 0.1 percent to about 5 percent by weight of the shampoo.

20. The composition set forth in claim 13, wherein the pediculocide agent is present in an amount not less than about 0.1 percent by weight of the carrier.

* * * * *